(12) United States Patent
Smith

(10) Patent No.: US 7,033,315 B2
(45) Date of Patent: *Apr. 25, 2006

(54) ENDOSCOPE AND ENDOSCOPIC INSTRUMENT SYSTEM HAVING REDUCED BACKLASH WHEN MOVING THE ENDOSCOPIC INSTRUMENT WITHIN A WORKING CHANNEL OF THE ENDOSCOPE

(75) Inventor: Kevin W. Smith, Coral Gables, FL (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/970,328

(22) Filed: Oct. 21, 2004

(65) Prior Publication Data

US 2005/0107662 A1    May 19, 2005

Related U.S. Application Data

(63) Continuation of application No. 10/214,005, filed on Aug. 7, 2002, now Pat. No. 6,881,186, which is a continuation of application No. 09/418,246, filed on Oct. 14, 1999, now Pat. No. 6,454,702.

(51) Int. Cl.
*A61B 1/00* (2006.01)
(52) U.S. Cl. .................... 600/104; 600/153
(58) Field of Classification Search ........ 600/104–106, 600/153–159
See application file for complete search history.

(56) References Cited

U.S. PATENT DOCUMENTS

| | | |
|---|---|---|
| 1,127,948 A | 2/1915 | Wappler |
| 2,036,528 A | 4/1936 | Kesling |
| 2,950,609 A | 8/1960 | Goodloe |
| 3,554,192 A | 1/1971 | Isberner |
| 3,805,770 A | 4/1974 | Okada |
| 3,895,636 A | 7/1975 | Schmidt |

(Continued)

FOREIGN PATENT DOCUMENTS

DE    28 29 159 A1    1/1980

(Continued)

OTHER PUBLICATIONS

Product Brochure, "TRIO 14, Re-Engineering Over-The-Wire Balloon Technology," 4 pages, 1994.

*Primary Examiner*—Beverly M. Flanagan
(74) *Attorney, Agent, or Firm*—Crompton, Seager & Tufte, LLC

(57) ABSTRACT

An endoscopic instrument has a portion having an outer surface with a non-circular cross-sectional shape. The non-circular cross-sectional shape may be provided to the instrument by providing peripheral projections or fins along the length of the portion or by providing the periphery of the portion with a polygonal shape. Where fins are used, the fins are preferably quite small and only have a minimal effect on the fluid flow cross sectional area between the interior of the working channel and the endoscopic instrument. The resulting instrument has significantly reduced backlash while maintaining adequate fluid flow in the working channel. According to a second embodiment of the invention, a portion of the interior of the working channel of the endoscope has an interior surface having a non-circular cross sectional shape by the inclusion of a plurality of radially spaced and inwardly directed ribs or by being polygonally shaped. The resulting endoscope reduces the backlash of an endoscopic instrument inserted therein while maintaining adequate fluid flow in the working channel.

19 Claims, 2 Drawing Sheets

U.S. PATENT DOCUMENTS

| | | |
|---|---|---|
| 3,955,578 A | 5/1976 | Chamness et al. |
| 4,046,150 A | 9/1977 | Schwartz et al. |
| 4,256,113 A | 3/1981 | Chamness |
| 4,294,254 A | 10/1981 | Chamness |
| 4,326,530 A | 4/1982 | Fleury, Jr. |
| 4,327,711 A | 5/1982 | Takagi |
| 4,345,599 A | 8/1982 | McCarrell |
| 4,430,083 A | 2/1984 | Ganz et al. |
| 4,493,320 A | 1/1985 | Treat |
| 4,503,855 A | 3/1985 | Maslanka |
| 4,590,938 A | 5/1986 | Segura et al. |
| 4,593,680 A | 6/1986 | Kubokawa |
| 4,619,260 A | 10/1986 | Magill et al. |
| 4,632,110 A | 12/1986 | Sanagi |
| 4,706,656 A | 11/1987 | Kuboto |
| 4,742,817 A | 5/1988 | Kawashima et al. |
| 4,763,668 A | 8/1988 | Macek et al. |
| 4,785,825 A | 11/1988 | Romaniuk et al. |
| 4,790,831 A | 12/1988 | Skribiski |
| D301,614 S | 6/1989 | Kozak et al. |
| 4,840,176 A | 6/1989 | Ohno |
| 4,840,623 A | 6/1989 | Quackenbush |
| 4,869,238 A | 9/1989 | Opie et al. |
| 4,872,456 A | 10/1989 | Hasson |
| 4,905,691 A | 3/1990 | Rydell |
| 4,945,920 A | 8/1990 | Clossick |
| 4,950,232 A | 8/1990 | Ruzicka et al. |
| 4,967,732 A | 11/1990 | Inoue |
| 4,973,321 A | 11/1990 | Michelson |
| 5,005,755 A | 4/1991 | Takahashi et al. |
| 5,026,371 A | 6/1991 | Rydell et al. |
| 5,059,199 A | 10/1991 | Okada et al. |
| 5,066,295 A | 11/1991 | Kozak et al. |
| 5,084,054 A | 1/1992 | Bencini et al. |
| 5,114,403 A | 5/1992 | Clarke et al. |
| 5,125,909 A | 6/1992 | Heimberger |
| 5,129,913 A | 7/1992 | Ruppert |
| 5,147,316 A | 9/1992 | Castillenti |
| 5,147,373 A | 9/1992 | Ferzil |
| RE34,110 E | 10/1992 | Opie et al. |
| 5,156,590 A | 10/1992 | Vilmar |
| 5,158,561 A | 10/1992 | Rydell et al. |
| 5,163,942 A | 11/1992 | Rydell |
| 5,176,677 A | 1/1993 | Wuchinich |
| 5,176,702 A | 1/1993 | Bales et al. |
| 5,179,935 A | 1/1993 | Miyagi |
| 5,183,470 A | 2/1993 | Wettermann |
| 5,201,740 A | 4/1993 | Nakao et al. |
| 5,201,743 A | 4/1993 | Haber et al. |
| 5,228,451 A | 7/1993 | Bales et al. |
| 5,244,619 A | 9/1993 | Burnham |
| 5,254,117 A | 10/1993 | Rigby et al. |
| 5,254,130 A | 10/1993 | Poncet et al. |
| 5,279,280 A | 1/1994 | Bacich et al. |
| 5,281,220 A | 1/1994 | Blake, III |
| 5,281,230 A | 1/1994 | Heidmueller |
| 5,290,294 A | 3/1994 | Cox et al. |
| 5,318,564 A | 6/1994 | Eggers |
| 5,334,169 A | 8/1994 | Brown et al. |
| 5,336,227 A | 8/1994 | Nakao et al. |
| 5,358,493 A | 10/1994 | Schweich, Jr. et al. |
| 5,366,443 A | 11/1994 | Eggers et al. |
| 5,376,094 A | 12/1994 | Kline |
| 5,403,342 A | 4/1995 | Tovey et al. |
| 5,404,887 A | 4/1995 | Prather |
| 5,406,939 A | 4/1995 | Bala |
| 5,439,478 A | 8/1995 | Palmer |
| 5,465,710 A | 11/1995 | Miyagi et al. |
| 5,486,182 A | 1/1996 | Nakao et al. |
| 5,496,292 A | 3/1996 | Burnham |
| 5,501,692 A | 3/1996 | Riza |
| 5,542,948 A | 8/1996 | Weaver et al. |
| 5,584,843 A | 12/1996 | Wulfman et al. |
| 5,588,964 A | 12/1996 | Imran et al. |
| 5,591,202 A | 1/1997 | Slater et al. |
| 5,601,533 A | 2/1997 | Hancke et al. |
| 5,636,634 A | 6/1997 | Kordis et al. |
| 5,642,736 A | 7/1997 | Avitall |
| 5,647,846 A | 7/1997 | Berg et al. |
| 5,681,296 A | 10/1997 | Ishida |
| 5,685,822 A | 11/1997 | Harhen |
| 5,685,853 A | 11/1997 | Bonnet |
| 5,718,360 A | 2/1998 | Green et al. |
| 5,741,271 A | 4/1998 | Nakao et al. |
| 5,746,747 A | 5/1998 | McKeating |
| 5,755,724 A | 5/1998 | Yoon |
| 5,759,187 A | 6/1998 | Nakao et al. |
| 5,762,631 A | 6/1998 | Klein |
| 5,766,217 A | 6/1998 | Christy |
| 5,769,841 A | 6/1998 | Odell et al. |
| 5,792,116 A | 8/1998 | Berg et al. |
| 5,800,444 A | 9/1998 | Ridinger et al. |
| 5,810,802 A | 9/1998 | Panescu et al. |
| 5,814,052 A | 9/1998 | Nakao et al. |
| 5,817,111 A | 10/1998 | Riza |
| 5,820,464 A | 10/1998 | Parlato |
| 5,820,546 A | 10/1998 | Ouchi |
| 5,827,177 A | 10/1998 | Oneda et al. |
| 5,827,272 A | 10/1998 | Breining et al. |
| 5,846,248 A | 12/1998 | Chu et al. |
| 5,860,975 A | 1/1999 | Goble et al. |
| 5,882,347 A | 3/1999 | Mouris-Laan et al. |
| 5,885,508 A | 3/1999 | Ishida |
| 5,906,620 A | 5/1999 | Nakao et al. |
| 5,906,621 A | 5/1999 | Secrest et al. |
| 5,951,579 A | 9/1999 | Dykes |
| 5,954,635 A | 9/1999 | Foley et al. |
| 5,957,932 A | 9/1999 | Bates et al. |
| 5,961,511 A | 10/1999 | Mortier et al. |
| 5,971,994 A | 10/1999 | Fritzsch |
| 5,984,904 A | 11/1999 | Steen et al. |
| 5,984,920 A | 11/1999 | Steinbach |
| 5,989,247 A | 11/1999 | Chambers |
| 5,993,474 A | 11/1999 | Ouchi |
| 6,001,096 A | 12/1999 | Bissinger et al. |
| 6,010,512 A | 1/2000 | Chu et al. |
| 6,015,381 A | 1/2000 | Ouchi |
| 6,015,415 A | 1/2000 | Avellanet |
| 6,024,708 A | 2/2000 | Bales et al. |
| 6,027,460 A | 2/2000 | Shturman |
| 6,050,995 A | 4/2000 | Durgin |
| 6,068,603 A | 5/2000 | Suzuki |
| 6,071,233 A | 6/2000 | Ishikawa et al. |
| 6,074,408 A | 6/2000 | Freeman |
| 6,090,073 A | 7/2000 | Gill |
| 6,090,129 A | 7/2000 | Ouchi |
| 6,093,195 A | 7/2000 | Ouchi |
| 6,224,611 B1 | 5/2001 | Ouchi |
| 6,235,026 B1 | 5/2001 | Smith |
| 6,299,612 B1 | 10/2001 | Ouchi |
| 6,409,727 B1 | 6/2002 | Bales et al. |
| 6,454,702 B1 | 9/2002 | Smith |
| 6,517,539 B1 | 2/2003 | Smith et al. |
| 6,537,205 B1 | 3/2003 | Smith |
| 6,761,717 B1 | 7/2004 | Bales et al. |
| 2003/0083545 A1 | 5/2003 | Smith |
| 2003/0125731 A1 | 7/2003 | Smith et al. |

FOREIGN PATENT DOCUMENTS

| | | |
|---|---|---|
| DE | 36 16 193 A1 | 11/1986 |
| DE | 94 18 834.3 U | 3/1995 |
| DE | 199 53 359 A1 | 5/2000 |

| | | | | | | |
|---|---|---|---|---|---|---|
| WO | WO 00/42926 | 7/1900 | | WO | WO 00/53107 | 9/2000 |
| WO | WO 92/22254 | 12/1992 | | WO | WO 01/10321 | 2/2001 |

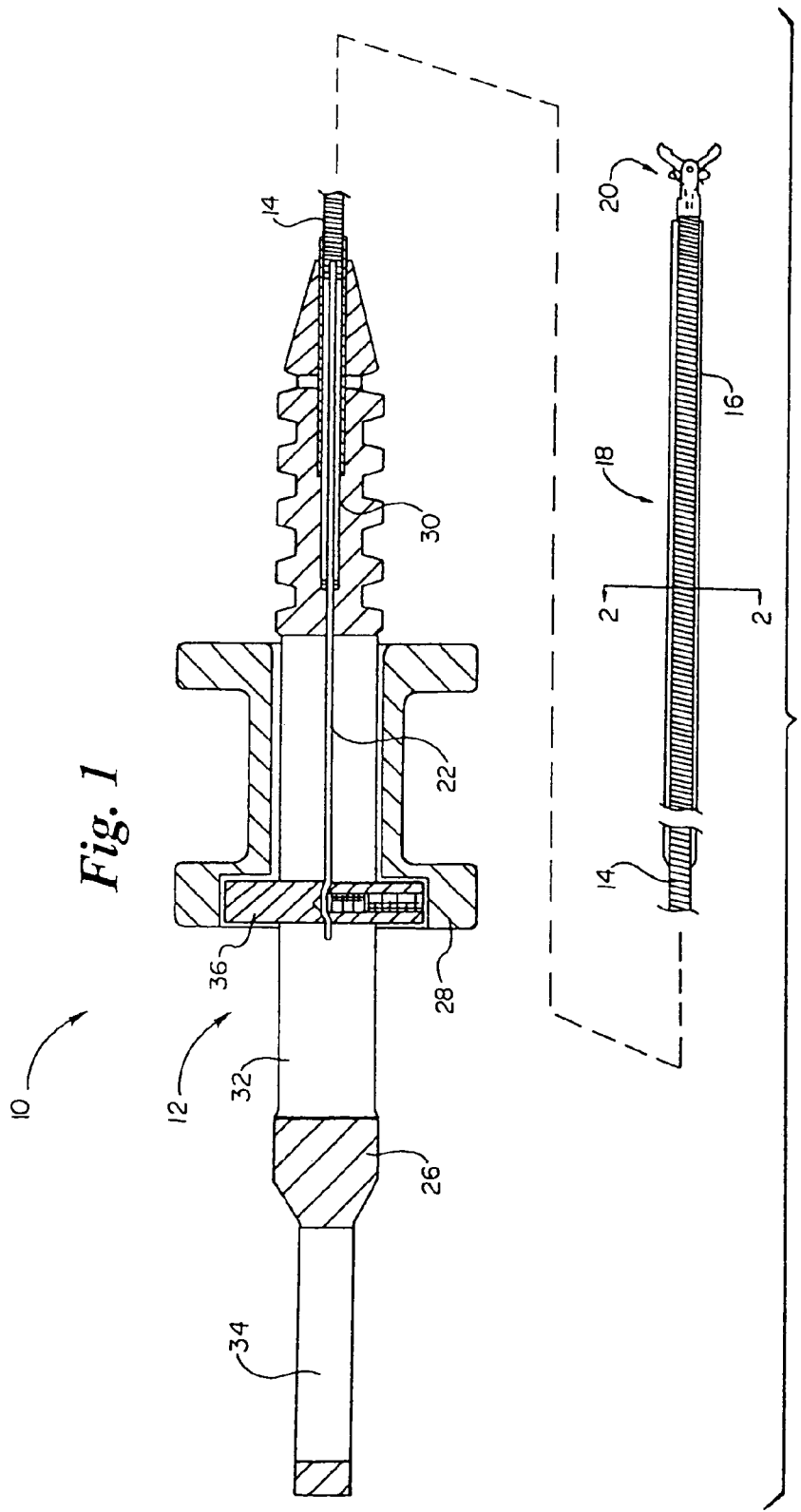
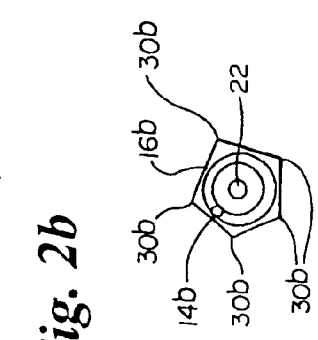
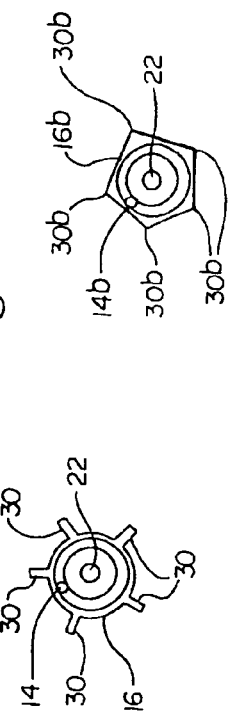
*Fig. 1*
*Fig. 2a*  *Fig. 2b*

ENDOSCOPE AND ENDOSCOPIC INSTRUMENT SYSTEM HAVING REDUCED BACKLASH WHEN MOVING THE ENDOSCOPIC INSTRUMENT WITHIN A WORKING CHANNEL OF THE ENDOSCOPE

CROSS REFERENCE OF CO-PENDING APPLICATIONS

This application is a continuation of U.S. application Ser. No. 10/214,005, filed Aug. 7, 2002 now U.S. Pat. No. 6,881,186, which is a continuation of U.S. application Ser. No. 09/418,246, filed Oct. 14, 1999, now U.S. Pat. No. 6,454,702, both disclosures of which are incorporated herein by reference.

FIELD OF THE INVENTION

This invention relates broadly to surgical instruments. More particularly, this invention relates to an endoscope and endoscopic surgical instruments adapted to be extended into a channel of the endoscope.

STATE OF THE ART

At the present time there are many instruments made for use in endoscopic medical procedures. Typically, endoscopic instruments are long and flexible cylindrically tubular devices with manually operated handles at their proximal ends and tissue-manipulative cutting, grasping, injecting, or cautery components at their distal ends. Such instruments are introduced into a flexible endoscope which is inserted into the patient through a natural or surgically-created opening. The endoscope includes an elongate portion defining several lumens therethrough and a proximal handle for directing the elongate portion. At least one lumen is provided with an optical imaging system, e.g., a scope, and several lumina or "working channels" are typically provided for extending endoscopic instruments therethrough. The working channel of the endoscope typically consists of a PTFE-lined cylindrical tube passing from the proximal (handle) end of the endoscope to its distal (working) end. Working channels are typically 2 to 4 millimeters in inside diameter.

During the medical procedure, the doctor passes one or more endoscopic instruments through the working channels in order to manipulate the tissue being visualized by the optical system of the endoscope. Usually the doctor must repeatedly manipulate the distal end of the instrument by manually pushing and pulling on the proximal portion of the tubular shaft of the endoscopic instrument near where the shaft enters the handle of the endoscope.

The view through an endoscope is highly magnified when seen on the video monitors typically used for these procedures; a field of view that may be a few millimeters across would be enlarged to several inches on the video screen. Accordingly, the instrument must be moved very precisely in very small increments in order to approximate and treat the tissue being visualized. In fact, the doctor must position the distal tip of the endoscopic instrument within a fraction of a millimeter of the desired location in order to achieve desired results. However, because of friction and backlash in the way the instrument passes through the endoscope, achieving this level of accuracy is difficult. For example, an endoscope several feet long may be positioned in the colon of a patient with the distal end of the endoscope tightly reflexed to visualize a particular area of the ascending colon. In such a position, the endoscope is bent into a very sinuous shape in multiple planes. Since the outside diameter of the endoscopic instrument is significantly smaller (e.g., 2.2 mm) than the inside diameter of the working channel (e.g., 3.2 mm), a large clearance space exists between the instrument and the channel. When the instrument is pulled back, the tension on the instrument causes the instrument to be pulled taut and the instrument naturally assumes the shortest path through the channel. When the instrument is pushed forward, friction causes it to assume the longest path through the channel (that is, the shaft of the instrument must "fill" the working channel before the distal end of the instrument begins to move). As a result, quite a bit of backlash (lost motion) is experienced by the doctor when the doctor tries to manipulate the distal end of the instrument. If it is necessary to pull the tip back a bit, the backlash must first be pulled out before the distal end can be retracted. If the doctor pulls the instrument back a little too far, the doctor must then push it several millimeters forward before there is any motion at all at the distal end. During this manipulation, the endoscopic instrument alternately assumes the longest-path and shortest-path positions within the working channel of the endoscope. If this backlash can be reduced or eliminated, the manipulation of the distal end of the endoscopic instrument can be made much easier and more positive, and the doctor can achieve his desired positioning more rapidly. However, this is not a simple problem to overcome for several reasons.

While the backlash situation described above can be reduced or substantially eliminated if the clearance between the outside of the endoscopic instrument and the inside of the working channel of the endoscope can be reduced, this is not a practical solution. It is often necessary to inject fluid (or to operate suction) through the annular space between these two structures. If the instrument shaft were to substantially fill up the space within the working channel, the backlash would be reduced, but there would be greatly reduced ability to conduct fluid through the working channel around the instrument. In fact, because of the nature of fluid flow, as the aspect ratio of the annular clearance space (the ratio of the thickness of the fluid channel to its circumferential length) becomes small, the impedance to fluid flow grows disproportionately to the reduction in cross-sectional area of the fluid passage.

In addition, as the diameter of the shaft approaches the inside diameter of the working channel, the area of contact between the instrument and the working channel becomes larger, particularly since the working channel is usually made of a relatively soft material, PTFE. This increase in contact area between these parts results in an increase in frictional drag on the instrument when the doctor attempts to move it through the channel.

SUMMARY OF THE INVENTION

It is therefore an object of the invention to provide an endoscopic system with little or no backlash between the endoscope and the endoscopic instrument.

It is also an object of the invention to provide an endoscopic system which reduces the backlash between an endoscopic instrument in a working channel of an endoscope, while maintaining open area therebetween for permitting fluid flow.

In accord with these objects, which will be discussed in detail below, an endoscopic system is provided where either a portion of the endoscopic instrument or a portion of the working channel is provided with a non-circular cross-section.

Generally, an endoscopic instrument includes an elongate flexible tubular member having proximal and distal ends, a control member having proximal and distal ends and extending through the tubular member, an end effector assembly coupled to the distal ends of the tubular member and the control member, and a handle means for moving the control member relative to the tubular member to operate the end effector assembly. According to a first embodiment of the invention, the distal end of the elongate flexible tubular member of the endoscopic instrument has an outer surface having a non-circular cross-sectional shape. The non-circular cross-sectional shape may be provided to the portion of the tubular member by radially spacing a plurality of fins or other projections about the peripheral (exterior) of the portion, or by providing the portion with a polygonal cross-sectional shape. Where fins are provided, the fins can be quite small and will only have a minimal effect on the fluid-flow cross-sectional area between the working channel and the endoscopic instrument. Thus, the resulting endoscopic instrument will have significantly reduced backlash while maintaining adequate fluid flow in the working channel. In addition, the fins or corners of the polygonal shape provide few and relatively small contact points so that the endoscopic instrument may be readily advanced through the lumen (working channel) of an endoscope.

According to a second embodiment of the invention, an endoscope is provided having a proximal handle, and elongate flexible distal portion having an imaging channel provided with an imaging system and a working channel having an interior surface and adapted to receive an endoscopic instrument therethrough. The working channel along its length has a preferably substantial portion at which the working channel has a non-circular cross-sectional shape. The non-circular cross-sectional shape can be provided to the working channel by providing the interior surface of the working channel with a plurality of radially spaced and inwardly directed ribs or other projections or by providing the interior surface of the working channel with a polygonal shape. The ribs can be quite small and will only have a minimal effect on the fluid flow cross sectional area between the working channel and the endoscopic instrument. Therefore, the resulting endoscope will reduce the backlash of an endoscopic instrument inserted therein while maintaining adequate fluid flow in the working channel. Additionally, the endoscopic instrument can be readily advanced through the working channel, as there will be few and relatively small contact points between the two.

Additional objects and advantages of the invention will become apparent to those skilled in the art upon reference to the detailed description taken in conjunction with the provided figures.

BRIEF DESCRIPTION OF THE DRAWINGS

FIG. 1 is a longitudinal cross sectional view of an endoscopic instrument according to the invention;

FIG. 2a is an enlarged cross-section across line 2—2 in FIG. 1 according to a first embodiment of the invention;

FIG. 2b is an enlarged cross-section across line 2—2 in FIG. 1 according to an alternative first embodiment of the invention;

DETAILED DESCRIPTION OF THE PREFERRED EMBODIMENTS

Figure 3:
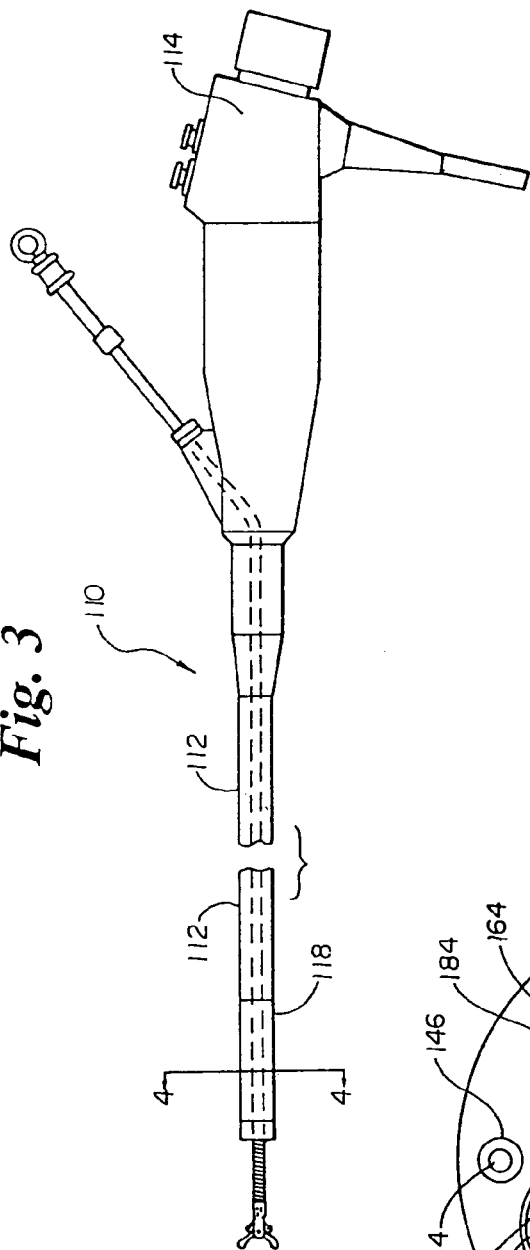
FIG. 3 is a side elevation of an endoscope according to the invention shown provided with an endoscopic instrument according to the invention.

Turning now to FIG. 1, an endoscopic instrument 10 for insertion through a working channel of an endoscope is shown. According to a first embodiment of the invention, the endoscopic instrument 10 includes an actuation handle 12, a tubular coil 14, a jacket 16 provided about at least a distal portion 18 of the coil 14, an end effector assembly 20, e.g., a biopsy forceps, and a control wire 22. The actuation handle 12 typically includes a stationary member 26 and a displaceable spool 28. The stationary member 26 includes a distal throughbore 30, a central slot 32, and a proximal thumb ring 34. The displaceable spool 28 is slidably disposed on the stationary member 26 and has a cross member 36 which passes through the slot 32. The proximal end of the control wire 22 is coupled to the spool 28. Operation of the actuation handle 12 is described fully in U.S. Pat. No. 5,228,451 to Bales, which is hereby incorporated by reference herein in its entirety. In brief, longitudinal movement of the spool 28 within the slot 32 results in operation of the end effector assembly 20; i.e., the end effector assembly moves between open and closed positions.

Referring now to FIGS. 1 and 2a, in accord with the first embodiment of the invention, the jacket 16 is a low friction coating or sheath, preferably made from PTFE, extending over at least a distal portion of the coil 14. The jacket 16 may be extruded over the portion of the coil, or may be provided as an attachment capable of being provided over an assembled endoscopic instrument. For example, the jacket may be a tubular member having a longitudinal slit. The jacket 16 defines several, e.g., five, longitudinal fins 30 radially spaced about the coil. By way of example, and not by limitation, for an endoscopic instrument intended to be inserted into an endoscope having a working channel of 3.2 mm inside diameter, the jacket 16 is preferably a cylinder 2.2 millimeters in diameter with thin fins (or lands) having a thickness of approximately 0.1 mm and extending approximately 0.4 mm out from the coil surface. Such a construction would almost completely fill the diameter of the working channel of the endoscope (i.e., the radial dimension of the jacket, from the center of the coil 14 out to the end of a fin 30, is nearly equal to the radius of the working channel), substantially reducing the motion backlash. However, since the fins 30 are quite thin, only a small amount of the fluid-flow cross sectional area would be sacrificed. Additionally, the number of the contact points and surface area of contact points between the fins and the interior of the working channel is substantially minimal.

It is also preferable that the fins extend along only a distal portion of the endoscopic instrument rather than along the entire length of the endoscopic instrument. If the fins 30 were to extend to the most proximal portion of the coil 14, it would be difficult to effect a fluid seal against the shaft of the instrument where the coil enters the endoscope handle. Such a seal is needed if fluid is to be injected through the working channel. Since the majority of the flexing of the endoscope in an endoscopic procedure takes place at the distal portion, where the endoscope is situated inside the patient, the majority of motion backlash results from the looseness of the instrument in the distal portion of the endoscope. Accordingly, it is preferable for the fins 30 to be placed on only the corresponding distal portion 18 of the endoscopic instrument 10 (for example, on the distal 150 cm of a 240 cm instrument) while leaving the proximal portion (i.e., 90 cm) a smooth cylinder. Such an endoscopic instrument would then have greatly reduced motion backlash when manipulated by the physician, and it would allow substantially unimpeded fluid flow through the working channel of the endoscope while providing an easily sealed-upon surface where the instrument exits the endoscope handle.

Turning now to FIG. 2b, according to an alternate first embodiment of the invention, the jacket 16b has a non-circular cross-sectional shape over the coil 14b such that the cross-sectional shape is generally polygonal. For example, the jacket 16b may have a pentagonal shape, as shown. By way of example, and not by limitation, for an endoscopic instrument intended to be inserted into an endoscope having a working channel of 3.2 mm inside diameter, the corners 30b of the polygon preferably extend approximately 0.4 mm from the coil surface. Such a construction substantially completely fills the diameter of the working channel of the endoscope, substantially reducing the motion backlash, yet only contacts the working channel at the corners 30b. In addition, space is provided between the sides of the jacket and the working channel for fluid-flow.

Figure 4:
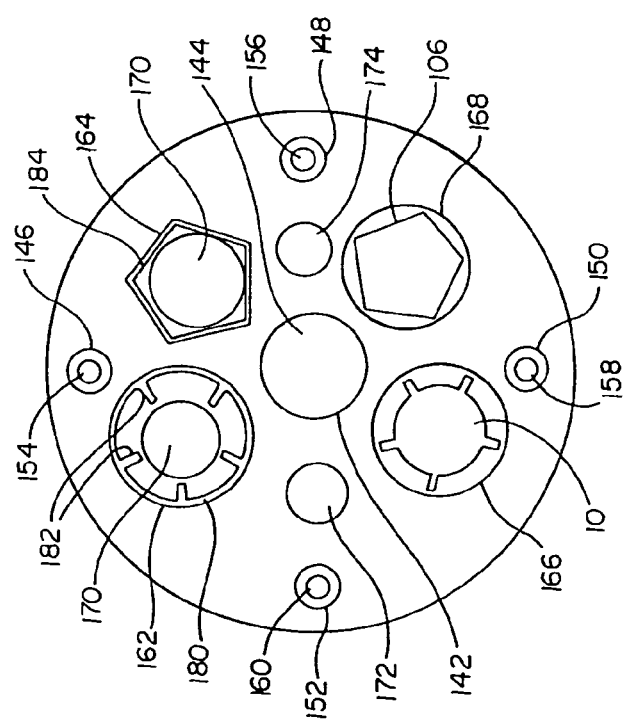
FIG. 4 is an enlarged cross-section across line 4—4 in FIG. 3, illustrating several working channel-endoscopic instrument systems according to the invention.

Referring now to FIGS. 3 and 4, an endoscope 110 according to a second embodiment of the invention is shown. The endoscope 110 includes an elongate tubular portion 112 and a proximal handle portion 114 adapted to manipulate and direct the distal end of the tubular portion 112. The tubular portion 112 has a plurality of lumens, with one lumen 142 provided for receiving an optical scope or camera device 144 (which may be built therein), several lumen 146, 148, 150, 152 provided for receiving control wires 154, 156, 158, 160 extending from the handle portion 114 through the tubular portion 112, and at least one, and preferably several working channels 162, 164, 166, 168 for receiving endoscopic instruments 170 therethrough. For example, endoscopic instruments 10, 10b according to the first embodiment of the invention (as shown in FIGS. 2a, and 2b, respectively) may be provided in working channels 166, 168. The working channels have proximal openings in the handle portion 114. Other lumens 172, 174 may be provided for other purposes. Endoscopes are described in general in U.S. Pat. No. 5,179,935 to Miyagi which is hereby incorporated by reference herein in its entirety.

According to the second embodiment of the invention, a portion of at least one of the working channels 162 is provided with a non-circular cross-sectional shape. The non-circular cross-sectional shape may be molded into the working channel or more preferably is provided by a low friction, e.g., PTFE, insert 180 preferably fixed within a distal portion 118 of the working channel 162. The insert 180 includes a plurality of radially spaced and radially inwardly directed longitudinal ribs 182. The ribs 182 can be quite small. For example, the ribs 182 may be approximately 0.1 mm thick and have a radial length of approximately 0.5 mm. Therefore, the ribs would have a minimal effect on the fluid flow cross sectional area between the working channel and the endoscopic instrument, and also provide relatively small contact points between the working channel and the endoscopic instrument.

According to an alternate second embodiment of the invention, a working channel 164 is provided with a polygonal cross-sectional shape. The polygonal cross-sectional shape may be provided to the working channel 164 via an insert 184 or may be molded integrally into the working channel.

In each of the alternate embodiments, the working channel is adapted to provide reduced backlash, while maintaining adequate fluid flow in the working channel around the endoscopic instrument, and minimal contact between the endoscopic instrument and the working channel. In each alternate embodiment, the non-circular cross-sectional shape of the working channel may extend the entire length of the channel or a portion thereof.

There have been described and illustrated herein several embodiments of an endoscope and endoscopic instrument system having reduced backlash when moving the endoscopic instrument within the working channel of the endoscope. While particular embodiments of the invention have been described, it is not intended that the invention be limited thereto, as it is intended that the invention be as broad in scope as the art will allow and that the specification be read likewise. Thus, while a particular biopsy forceps endoscopic instrument has been disclosed, it will be appreciated that endoscopic instruments having other end effectors, e.g., scissors, punches, needles, etc., can be provided with the non-circular cross-section of the invention as well. Furthermore, while a PTFE has been disclosed for the jacket of the instruments and insert for the endoscope, other low friction materials can be used as well. Also, while a particular number of fins and ribs have been disclosed, it will be appreciated that other numbers of fins and ribs can be used. Alternatively, one or spiral fins or ribs can be provided. Furthermore, projections other than fins can be used. Moreover, other polygonal shapes may be used for the jacket over the coil and the endoscope insert. Also, the coil and/or jacket may be substituted with another tubular member having a non-circular cross-section. For example, the tubular member may be extruded with a polygonal shape or with fins. It will therefore be appreciated by those skilled in the art that yet other modifications could be made to the provided invention without deviating from its spirit and scope as so claimed.

What is claimed is:

1. An endoscopic instrument, comprising:
   an endoscope having a working channel formed therein, the working channel defining an inside diameter; and
   an endoscopic instrument slidably disposed in the working channel, the endoscopic instrument including:
      a tubular member including a region having a non-circular cross-sectional shape and a section having an outside diameter that is substantially equal to the inside diameter of the working channel,
      a control member slidably disposed in the tubular member with an end effector coupled to the control member; and
      a handle disposed adjacent a proximal end of the control member for controlling the position of the end effector.

2. The endoscopic instrument of claim 1, wherein the tubular member includes a proximal portion and a distal portion and wherein the region having a non-circular cross-section shape is disposed adjacent the distal portion.

3. The endoscopic instrument of claim 2, wherein the proximal portion has a generally circular cross-sectional shape.

4. The endoscopic instrument of claim 1, wherein the region having a non-circular cross-section shape has a polygonal shape.

5. The endoscopic instrument of claim 1, wherein the region having a non-circular cross-section shape is defined by a sheath disposed over a portion of the tubular member.

6. The endoscopic instrument of claim 5, wherein the sheath includes a plurality of fins extending therefrom.

7. The endoscopic instrument of claim 1, wherein the working channel includes a region having a non-circular cross-section shape.

8. An endoscopic instrument system, comprising:
- an endoscope having a working channel, an inside surface defining a working channel, and an inside diameter defined within the working channel;
- an elongate tubular member slidably disposed in the working channel, the tubular member having an outside surface having a section with an outside diameter that is substantially equal to the inside diameter of the working channel;
- wherein at least one of the inside surface of the endoscope and the outside surface of the tubular member includes a region having a generally non-circular cross-sectional shape;
- a control member slidably disposed in the tubular member;
- an end effector coupled to the control member; and
- a handle disposed coupled the control wire for altering the position of the end effector.

9. The endoscopic instrument of claim 8, wherein the inside surface of the endoscope includes the region having a generally non-circular cross-sectional shape.

10. The endoscopic instrument of claim 8, wherein the outside surface of the tubular member includes the region having a generally non-circular cross-sectional shape.

11. The endoscopic instrument of claim 8, wherein both the inside surface of the endoscope and the outside surface of the tubular member include regions having a generally non-circular cross-sectional shape.

12. A medical device, comprising:
- a first tubular member having an inside diameter and an inside wall surface, the inside wall surface defining a channel through the first tubular member; and
- a second tubular member slidably disposed in the channel, the second tubular member including an outer surface having a region with a non-circular cross-sectional shape and a section having an outside diameter that is substantially equal to the inside diameter of the first tubular member, an inner surface defining a lumen through the second tubular member and a shaft slidably disposed in the lumen.

13. The medical device of claim 12, wherein the second tubular member includes a proximal portion and a distal portion and wherein the region having a non-circular cross-section shape is disposed adjacent the distal portion.

14. The medical device of claim 13, wherein the proximal portion has a generally circular cross-sectional shape.

15. The medical device of claim 14, wherein the region having a non-circular cross-section shape has a polygonal shape.

16. The medical device of claim 13, wherein the region having a non-circular cross-section shape is defined by a sheath disposed over a portion of the second tubular member.

17. The medical device of claim 16, wherein the sheath includes a plurality of fins extending therefrom.

18. The medical device of claim 13, wherein the working channel includes a region having a non-circular cross-section shape.

19. A medical device, comprising:
- a first tubular member having a working channel, an inside surface defining a working channel, and an inside diameter defined within the working channel;
- a second tubular member slidably disposed in the working channel, the second tubular member having an outside surface having a section with an outside diameter that is substantially equal to the inside diameter of the working channel;
- wherein at least one of the inside surface of the first tubular member and the outside surface of the second tubular member includes a region having a generally non-circular cross-sectional shape;
- a control member slidably disposed in the second tubular member;
- an end effector coupled to the control member; and
- a handle disposed coupled the control wire for altering the position of the end effector.

* * * * *

UNITED STATES PATENT AND TRADEMARK OFFICE
CERTIFICATE OF CORRECTION

| | | |
|---|---|---|
| PATENT NO. | : 7,033,315 B2 | Page 1 of 1 |
| APPLICATION NO. | : 10/970328 | |
| DATED | : April 25, 2006 | |
| INVENTOR(S) | : Kevin W. Smith | |

It is certified that error appears in the above-identified patent and that said Letters Patent is hereby corrected as shown below:

Column 3
Line 25, delete "comers" and insert therefor -- corners --.

Column 5
Line 22, delete "comers" and insert therefor -- comers --.

Signed and Sealed this

Twenty-second Day of August, 2006

JON W. DUDAS
*Director of the United States Patent and Trademark Office*